(12) United States Patent
Sabnis et al.

(10) Patent No.: US 7,906,130 B2
(45) Date of Patent: *Mar. 15, 2011

(54) AMITRAZ COMPOSITIONS

(75) Inventors: Shobhan Shashi Sabnis, Pennington, NJ (US); Jacob A. Zupan, Yardley, PA (US); Robert Bruce Albright, Chalfont, PA (US)

(73) Assignee: Wyeth LLC, Madison, NJ (US)

( * ) Notice: Subject to any disclaimer, the term of this patent is extended or adjusted under 35 U.S.C. 154(b) by 1537 days.

This patent is subject to a terminal disclaimer.

(21) Appl. No.: 11/245,579

(22) Filed: Oct. 7, 2005

(65) Prior Publication Data

US 2006/0078585 A1 Apr. 13, 2006

Related U.S. Application Data

(60) Provisional application No. 60/683,646, filed on May 23, 2005, provisional application No. 60/616,995, filed on Oct. 8, 2004.

(51) Int. Cl.
*A01N 25/00* (2006.01)
*A01N 33/18* (2006.01)
*A01N 33/24* (2006.01)
*A01N 31/04* (2006.01)
*C07C 281/00* (2006.01)
*C07D 307/02* (2006.01)

(52) U.S. Cl. .......... 424/405; 514/741; 564/36; 549/295

(58) Field of Classification Search .......... 424/405; 514/28, 65, 241, 594, 590, 617, 741; 564/36; 549/295

See application file for complete search history.

(56) References Cited

U.S. PATENT DOCUMENTS

| | | | |
|---|---|---|---|
| 4,560,553 A | 12/1985 | Zupan | |
| 4,710,512 A | 12/1987 | Webb | |
| 5,116,850 A | 5/1992 | Stevenson | |
| 5,304,573 A | 4/1994 | Hino et al. | |
| 5,324,837 A | 6/1994 | Renga et al. | |
| 5,462,938 A | 10/1995 | Annus et al. | |
| 5,543,573 A | 8/1996 | Takagi et al. | |
| 5,708,170 A | 1/1998 | Annis et al. | |
| 5,965,137 A | 10/1999 | Petrus | |
| 5,968,990 A | 10/1999 | Jon et al. | |
| 6,387,933 B1 * | 5/2002 | Nakamura et al. | 514/345 |
| 6,955,818 B1 | 10/2005 | Hacket et al. | |
| 7,749,527 B2 * | 7/2010 | Fattohi et al. | 424/407 |
| 7,763,267 B2 * | 7/2010 | Albright et al. | 424/407 |
| 2004/0116419 A1 * | 6/2004 | Heaney et al. | 514/229.2 |
| 2004/0122075 A1 | 6/2004 | Chiarello et al. | |

FOREIGN PATENT DOCUMENTS

| | | |
|---|---|---|
| EP | 0 036 138 A2 | 9/1981 |
| EP | 1413201 A2 | 4/2004 |
| EP | 1334661 B1 | 1/2007 |
| JP | 08268994 | 10/1996 |
| JP | 09301947 | 11/1997 |
| WO | WO 92/06076 A1 | 4/1992 |
| WO | WO 96/10560 A1 | 4/1996 |
| WO | WO 00/54591 A2 | 9/2000 |
| WO | WO 01/01781 A1 | 1/2001 |
| WO | WO 2006/002984 A1 | 1/2006 |
| WO | WO 2006/042099 A1 | 4/2006 |

OTHER PUBLICATIONS

Remington, Joseph P., "Remington: The Science and Practice of Pharmacy", 19$^{th}$ Edition, 1995 p. 1583.
Payne et al. "Structure-Activity relationships for the action of dihydropyrazole insecticides on mouse brain sodium channels", Pesticide Biochemistry and Physiology, 1998, vol. 60 pp. 177-185.
Wing et al., "A novel oxadiazine insecticide is bioactivated in lepidopteran larvae", Archives of Insect Biochemistry and Physiology, 1998, vol. 37(91) pp. 91-103.
Package Insert Frontline Top Spot® for Dogs, Merial Limited, purchased Jan. 31, 2008.

\* cited by examiner

*Primary Examiner* — Johann R Richter
*Assistant Examiner* — Mei-Ping Chui
(74) *Attorney, Agent, or Firm* — Joel Silver

(57) ABSTRACT

The present invention provides a stable composition which comprises a non-hydroxyl-group-containing solvent mixture comprising N,N-diethyl-m-toluamide and γ-hexalactone, optionally with dimethyl sulfoxide, eucalyptol and 1-methoxy-2-propyl acetate; and an effective amount of each of amitraz and at least one additional parasiticidal compound, such as R-28153. Said composition allows for high concentrations of a mixture of parasiticidal agents in a single application and is useful for treating and controlling parasiticidal infection and infestation in a homeothermic animal.

20 Claims, No Drawings

AMITRAZ COMPOSITIONS

This application claims the benefit under 35 U.S.C. §119 (e) to U.S. provisional application No. 60/616,995, filed Oct. 8, 2004, and U.S. provisional application No. 60/683,646, filed May 23, 2005 each of which is hereby incorporated by reference in its entirety.

BACKGROUND OF THE INVENTION

Amitraz is a valuable veterinary product effective against strains of ticks resistant to other chemical classes of ixodicides. It also possesses sufficient persistence on hair and wool to control all stages of parasitic ticks. The unique expellent action of amitraz causes ticks to withdraw mouthparts rapidly from, and fall off, the host animal. Effective tick control in conjunction with effective ecto or endoparasiticidal control is highly desirable in the raising, breeding and housing of healthy agronomic and domestic animals. Amitraz is, unfortunately, chemically unstable in the presence of solvents having a reactive hydroxyl group such as alcohols, glycols, water and the like. This characteristic has limited the development of veterinary compositions containing amitraz, and especially those containing amitraz and at least one additional parasiticidal agent, due to the combination of the instability of amitraz in hydroxyl-group-containing solvents and the insolubility of many parasiticidal agents in non-hydroxyl-group-containing solvents.

A further complication to the formulation of amitraz-containing compositions for use with animals is the cosmetic acceptability and non-irritability of the formulation when applied to the animal. Obviously, an acceptable formulation must be sufficiently easy to apply, dry within a reasonable period of time without impairment of the animal's appearance, be gentle on the animal's coat, non-irritating to the animal's skin and maintain its effectiveness on the animal through normal activities of the animal, such as exposure to sun and water. It must also be able to be applied to the animal in a small enough volume so that it can be applied so as to avoid the animal licking the area of application. Most desirably, the composition will provide the active ingredients in a formulation which will have at least a sufficient duration of activity, so as to avoid the necessity of frequent reapplication during this period of time.

Therefore, it is an object of this invention to provide a topical, parasiticidal veterinary composition containing amitraz, and at least one additional parasiticidal compound, which is stable, and which allows sufficiently high concentrations of each of the active ingredients.

It is likewise an object of the invention to provide a composition which provides for at least a one-month interval between applications.

It is another object of the invention to provide a method for the prevention, treatment and control of ectoparasiticidal infection or infestation in an animal, particularly a homeothermic animal.

An additional feature of this invention is that the compositions provided offer improved efficacy over a broad spectrum of parasites for an extended period of time.

Other objects and features of the invention will be come more apparent from the detailed description set forth hereinbelow.

SUMMARY OF THE INVENTION

The present invention provides a composition which comprises an effective amount of each of amitraz and at least one additional parasiticidal compound in a non-hydroxyl-group-containing solvent mixture comprising N,N-diethyl-m-toluamide and γ-hexalactone. In a preferred composition, the non-hydroxyl-group-containing solvent mixture additionally comprises: dimethyl sulfoxide; eucalyptol; and 1-methoxy-2-propyl acetate.

Also provided are a method for the treatment and control of parasitic infection and infestation and a process for the preparation of a topical veterinary parasiticidal composition.

DETAILED DESCRIPTION OF THE INVENTION

Many topical veterinary compositions require relatively high concentrations of active ingredients to ensure effective and long-lasting protection to the host animal and administration in sufficiently small volumes so as to avoid loss of the composition from run-off or licking by the animal. Typical "spot-on" applications of such compositions to the base of the neck of the animal aid in making the applied composition difficult for the animal to remove, but require that a relatively small volume be applied. Frequently, highly polar solvents containing active hydroxyl groups such as water, alcohol, glycol or the like are utilized to prepare such compositions due to their compatibility with animal skin, hide and/or hair, and their ability to dissolve relatively high concentrations of active. Topical veterinary compositions containing amitraz as one of the active ingredients are highly desirable due to the effective and persistent activity of amitraz against a wide variety of ticks, including ticks resistant to other parasiticidal actives. Heretofore, veterinary compositions containing amitraz and an additional parasiticidal compound have been limited by the instability of amitraz in the presence of hydroxyl-group-containing solvents.

Surprisingly, it has now been found that amitraz and at least one additional parasiticidal compound may be formulated in a stable topical non-irritating composition by employing as a carrier a non-hydroxyl-group-containing solvent combination of N,N-diethyl-m-toluamide and γ-hexalactone, optionally, in further combination with dimethyl sulfoxide, eucalyptol, and 1-methoxy-2-propyl acetate. Accordingly, the present invention provides a topical veterinary parasiticidal composition which comprises a non-hydroxyl-group-containing solvent mixture comprising N,N-diethyl-m-toluamide and γ-hexalactone, optionally with dimethyl sulfoxide, eucalyptol, and 1-methoxy-2-propyl acetate; and an effective amount of each of amitraz and at least one additional parasiticidal compound.

Solvent mixtures suitable for the composition of the invention include those non-hydroxyl-group-containing solvent mixtures containing about 2-30% w/v, preferably about 5-25% w/v of N,N-diethyl-m-toluamide; about 2-30% w/v, preferably about 5-25% w/v, of dimethyl sulfoxide; about 2-30% w/v, preferably about 5-25% w/v, of eucalyptol; about 2-40% w/v, preferably about 10-30% w/v, of γ-hexalactone, and about 2-40% w/v, preferably about 15-35% w/v, of 1-methoxy-2-propyl acetate.

The effective amounts of amitraz and at least one additional parasiticidal compound may be up to as high as 30% w/v of the total composition. For example, amitraz may be present at about 10-30% w/v, preferably 13-20% w/v, and the additional parasiticidal compounds may be present at about 10-30% w/v, preferably 13-20% w/v. The effective amounts of the additional parasiticidal compounds may vary according to the potency of the compounds, the method of application, the host animal, the target parasite, the degree of infestation, or the like. It is understood that effective amounts of less than 10% of the additional parasiticidal compounds may be suitable for the composition of the invention. For example when the composition is administered in the form of a pour-on, spray or any topical administration suitable for use in large animals such as swine, sheep, horses or cattle, amounts of about 3-9% w/v, preferably 5-7% w/v, of amitraz may be suitable and amounts of about 3-9% w/v, preferably 5-7% w/v, of the additional parasiticidal compound may be suitable.

Examples of non-hydroxyl-group-containing solvents include: N,N-diethyl-m-toluamide, γ-hexalactone, dimethyl sulfoxide, eucalyptol, D-limonene, 1-methoxy-2-propyl acetate, diethylene glycol monobutyl ether acetate, diethylene glycol monoethyl ether acetate, propylene glycol diacetate, ethylene glycol butyl ether acetate, N-methyl-2-pyrrolidone, benzyl acetate, dimethyl formamide, diethyl succinate, diethyl adipate, diethyl sebacate, 2,6-dimethyl-4-heptanone, dipropylene glycol dimethyl ether, heptyl acetate, 2-butoxyethyl acetate, isopropyl myristate, lauryl pyrrolidone, methyl butanone, methyl pentanone, alkylethers of ethylene glycol, γ-butyrolactone, benzyl benzoate, and the like; preferably N,N-diethyl-m-toluamide, γ-hexalactone, dimethyl sulfoxide, eucalyptol, 1-methoxy-2-propyl acetate, or a mixture thereof.

Representative parasiticidal compounds suitable for use in the composition of the invention are: chitin synthesis inhibitors including benzoylphenylureas such as diflubenzuron, flufenoxuron, teflubenzuron, novaluron, fluazuron, or the like; juvenile hormone mimics such as methoprene, hydroprene, pyriproxyfen, fenoxycarb, or the like; pyrethroid insecticides such as permathrin, cypermethrin, α-cypermethrin or the like; phenylpyrazole insecticides such as fipronil; organophosphate insecticides such as chlorfenvinphos, diazinon, malathion, terbufos, or the like; oxime carbamate insecticides; avermectins such as abamectin, doramectin, ivermectin, selamectin or eprinomectin; imidacloprid; milbemycins such as moxidectin or milbemycin oxime; semicarbazones such as endoxcarb or R-28153, preferably R-28153 (also named as metaflumizone); and the like. R-28153 is especially preferred for use with amitraz, due to its complementary mode of parasiticidal activity, and its chemical compatibility with, and solubility in, non-hydroxyl-group-containing solvents.

As used in the specification and claims, the term R-28153 designates the compound 2-[2-(4-cyanophenyl)-1-[3-(trifluoromethyl) phenyl]ethylidene]-N-[4-(trifluoromethoxy) phenyl]-hydrazinecarboxamide. R-28153 and a method for the preparation thereof are described in U.S. Pat. No. 5,543, 573. The animal health uses of R-28153 are described in U.S. Patent Publication number US 2004-0116419A1.

As used herein, the term "w/w" designates weight/weight, the term "w/v" designates weight/volume, and the term "mg/kg" designates milligrams per kilogram of body weight.

Advantageously, the stable topical parasiticidal veterinary composition of the invention allows for high concentrations of the active ingredients and demonstrates no irritation to the skin/hide/hair of the host animal. Accordingly, the present invention provides a method for the treatment and control of ectoparasiticidal infection or infestation in an animal, particularly a homeothermic animal, which comprises topically administering to said animal a composition which comprises a non-hydroxyl-group-containing solvent mixture comprising N,N-diethyl-m-toluamide and γ-hexalactone; optionally with dimethyl sulfoxide; eucalyptol; and 1-methoxy-2-propyl acetate; and an effective amount of each of amitraz and at least one additional parasiticidal compound.

Examples of topical administrations suitable for use in the method of the invention include spot-on, pour-on, dip, wash, shampoo, foam, gel, lotion, or any of the conventional means of topically applying a liquid veterinary composition. The topical mode or administration will vary with the species and size of the host animal. As an example, for companion animals such as dogs or cats, a spot-on, gel, shampoo or wash, and most preferably a spot-on, may be suitable. For large agronomic animals such as cattle, horses or sheep, a pour-on or spray, most preferably a pour-on, may be suitable.

Homeothermic animals suitable for treatment using the composition and method of the present invention include: swine, cattle, sheep, horses, goats, camels, water buffalos, donkeys, rabbits, fallow deer, reindeer, minks, chinchillas, raccoons, chicken, geese, turkeys, ducks, dogs, cats, or the like, preferably dogs, cats, swine, cattle, horses or sheep.

Ectoparasitic infection or infestations suitable for treatment by the method of the invention include fleas, ticks, lice, mites and flies.

In actual practice, the composition of the invention may be administered in dose rates of mg of active ingredient per kg of body weight of the host animal. Dose rates suitable for use in the method of invention will vary depending upon the mode of administration, the species and health of the host animal, the target parasite, the degree of infection or infestation, the breeding habitat, the potency of the additional parasiticidal compound, and the like. In general, a dose of at least 20 mg/kg of amitraz is suitable and, in the case wherein the additional parasiticidal compound is R-28153, at least 1.0 mg/kg of R-28153, preferably 20-45 mg/kg of amitraz and 20-45 m/kg of R-28153.

In one embodiment of the invention, a dose rate of about 0.1-100 mg/kg, preferably about 1.0-50 mg/kg, of amitraz may be suitable and about 0.1-100 mg/kg, preferably about 1.0-50 mg/kg of an additional parasiticidal compound, such as R-2813. Such doses may be particularly applicable to large animals such as swine, cattle, horses or sheep.

The present invention also provides a process for the preparation of a topical veterinary parasiticidal composition which comprises: admixing N,N-diethyl-m-toluamide and γ-hexalactone, optionally with dimethyl sulfoxide, eucalyptol, and 1-methoxy-2-propyl acetate to form a non-hydroxyl-group-containing solvent mixture; and treating said solvent mixture with amitraz and at least one additional parasiticidal compound to form a homogeneous solution, optionally passing said solution through a solid dehydrating agent.

Parasiticidal compounds suitable for use in the process of the invention may be chitin synthesis inhibitors including benzoylphenylureas such as diflubenzuron, flufenoxuron, teflubenzuron, novaluron, fluazuron, or the like; juvenile hormone mimics such as methoprene, hydroprene, pyriproxyfen, fenoxycarb, or the like; pyrethroid insecticides such as permathrin, cypermethrin, α-cypermethrin or the like; phenylpyrazole insecticides such as fipronil; organophosphate insecticides such as chlorfenvinphos, diazinon, malathion, terbufos, or the like; oxime carbamate insecticides; avermectins such as abamectin, doramectin, ivermectin, selamectin or eprinomectin; imidacloprid; milbemycins such as moxidectin or milbemycin oxime, semicarbazones such as endoxcarb or R-28153; and the like, preferably R-28153.

Solid dehydrating agents suitable for use in the process of the invention include any conventional solid reagents useful for absorbing and removing trace amounts of water from a solution, for example silica gel, magnesium sulfate, sodium sulfate, charcoal, molecular sieves, or the like, preferably molecular sieves, more preferably 4 Å molecular sieves.

For a more clear understanding of the invention, the following examples are set forth hereinbelow. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

Example 1

Preparation of Ectoparasiticidal Compositions

| Component Description | A w/w % | A w/v % | B w/w % | B w/v % |
|---|---|---|---|---|
| amitraz | 14.6 | 15.3 | 14.6 | 15.3 |
| R-28153 | 14.6 | 15.3 | 14.6 | 15.3 |
| N,N-diethyl-m-toluamide | 9.6 | 10.0 | 9.6 | 10.0 |
| dimethyl sulfoxide | 9.6 | 10.0 | 9.6 | 10.0 |
| eucalyptol | 9.6 | 10.0 | 9.6 | 10.0 |
| 1-methoxy-2-propyl acetate | 28.7 | 30.0 | 19.1 | 20.0 |
| γ-hexalactone | 13.3 | 9.4 | 22.9 | 19.4 |

Method of Preparation

The following solvents are introduced sequentially into a jacketed vessel at 25° C. with stirring: N,N-diethyl-m-toluamide, dimethyl sulfoxide, eucalyptol, 1-methoxy-2-propyl acetate and γ-hexalactone. This solvent mixture is slowly treated with R-28153 and amitraz; stirring is continued until solution is complete. The resultant solution is passed through a bed of activated 4 Å molecular sieves.

Example 2

Preparation of Ectoparasiticidal Compositions

Using essentially the same procedure described in Example 1 hereinabove, the compositions shown below are prepared.

| Component Description | C w/w % | D w/w % |
|---|---|---|
| amitraz | 14.5 | 14.5 |
| R-28153 | 14.5 | 14.5 |
| N,N-diethyl-m-toluamide | 19.3 | 9.6 |
| dimethyl sulfoxide | — | 9.6 |
| eucalyptol | 9.6 | 19.3 |
| 1-methoxy-2-propyl acetate | 22.8 | 32.5 |
| γ-hexalactone | 14.5 | — |
| Silwet ®-560 organosilicone | 4.8 | — |

Example 3

Preparation of Ectoparasiticidal Compositions

Using essentially the same procedure described in Example 1 hereinabove, the compositions shown below are prepared.

| Component Description | E w/v % | F w/v % |
|---|---|---|
| amitraz | 6.0 | 6.0 |
| R-28153 | 6.0 | 6.0 |
| N,N-diethyl-m-toluamide | 10.0 | 10.0 |
| eucalyptol | 10.0 | 10.0 |
| 1-methoxy-2-propyl acetate | 30.0 | 20.0 |
| γ-hexalactone | 38.8 | 48.0 |

Example 4

Evaluation of the Efficacy of Test Composition B

In this evaluation sixteen dogs are each infested with 100 unfed adult fleas (*Ctenocephalides felis*) and 50 adult brown dog ticks (*Rhipicephalus sanguineus*). Each dog is assessed for its ability to retain fleas and ticks by examination and combing taken 24 hours post infestation for fleas and 48 hours post infestation for ticks. The dogs are blocked by flea counts and randomly assigned to one of two treatment groups. Two days prior to treatment each dog is infested with 50 adult brown dog ticks and 50 adult American dog ticks (*Dermacentor variables*). One day prior to treatment each dog is infested with 100 fleas. Test composition B is applied at a dose rate of 20 mg/kg of amitraz and 20 mg/kg of R-28153 to a single spot on the skin between the shoulder blades of the dogs in one group. The other group is not treated. At one-day post treatment, the live fleas and ticks on the dogs are counted to check for knockdown efficacy. At two days post treatment, the dogs are examined and combed to count and remove live fleas and ticks. The dogs are subsequently re-infested with fleas and both species of ticks, and examined and comb counted at weekly intervals. Efficacy of the test composition is determined relative to the untreated dogs, and is recorded as a percent of the geometric mean of the insect count for the untreated control animals. The data obtained is shown in Table I below where DAT designates days after treatment.

TABLE I

| | % Efficacy of Composition B | | |
|---|---|---|---|
| DAT | Fleas | Brown Dog Ticks | American Dog Ticks |
| 1 | 99.4 | 97.4 | 97.6 |
| 2 | 100 | 99.7 | 100 |
| 7 | 100 | 100 | 100 |
| 14 | 99.6 | 100 | 100 |
| 21 | 100 | 96.5 | 96.3 |
| 28 | 98.8 | 86.5 | 89.8 |
| 35 | 95.9 | 34.5 | 43.3 |
| 42 | 86.6 | 17.3 | 21.8 |

As can be seen from the data shown hereinabove, the composition of the invention is stable and efficacious over an extended period of time.

Example 5

Evaluation of the Efficacy of Test Compositions E and F

In this evaluation, swine are separated into control groups and treatment groups. The control (untreated) and treatment groups are housed separately. Each treatment group is treated with sufficient test composition to obtain doses of 1.0 mg/kg, 15 mg/kg, 30 mg/kg and 50 mg/kg, i.e. a total of eight treatment groups made up of 4 dose rates for each test compound. For each treatment group, the test compound is poured on the back of the swine. Fly counts are made for all groups at time 0, 7 days after treatment and weekly thereafter. Efficacy of the test composition is determined relative to the untreated swine, and is recorded as a percent of the geometric mean of the fly count for the untreated control animals.

What is claimed is:

1. A composition which comprises a non-hydroxyl-group-containing solvent mixture comprising N,N-diethyl-m-toluamide and γ-hexylactone, optionally with dimethyl sulfoxide, eucalyptol and 1-methoxy-2-propyl acetate; and an effective amount of each of amitraz and 2-[2-(4-cyanophenyl)-1-[3-(trifluoromethyl)phenyl]ethylidene]-N-[4-(trifluoromethoxy)phenyl]-hydrazinecarboxamide (R-28153).

2. The composition according to claim 1 wherein the solvent mixture comprises about 2-30% w/v of N,N-diethyl-m-toluamide; 2-30% w/v of dimethyl sulfoxide; 2-30% w/v of eucalyptol; 2-40% w/v of γ-hexylactone, and 2-40% w/v of 1-methoxy-2-propyl acetate.

3. The composition according to claim 1 wherein the effective amount is about 10-30% w/v of amitraz and about 10-30% w/v of R-28153.

4. The composition according to claim 1 wherein the effective amount is about 3-9% w/v of amitraz and about 3-9% w/v of R-28153.

5. The composition according to claim 3 wherein the effective amount is about 13-20% w/v of amitraz and about 13-20% w/v of R-28153.

6. The composition according to claim 4 wherein the effective amount is about 5-7% w/v of amitraz and about 5-7% w/v of R-28153.

7. The composition according to claim 5 wherein the solvent mixture is about 5-25% w/v of N,N-diethyl-m-toluamide; 5-25% w/v of dimethyl sulfoxide; 5-25% w/v of eucalyptol; 10-30% w/v of γ-hexylactone; and 15-35% w/v of 1-methoxy-2-propyl acetate.

8. A method for the treatment and control of ectoparasiticidal infection or infestation in a homeothermic animal which comprises topically administering to said animal a composition, which comprises a non-hydroxyl-group-containing solvent mixture comprising N,N-diethyl-m-toluamide and γ-hexylactone, optionally with dimethyl sulfoxide, eucalyptol and 1-methoxy-2-propyl acetate; and an effective amount of each of amitraz and 2-[2-(4-cyanophenyl)-1-[3-(trifluoromethyl)phenyl]ethylidene]-N-[4-(trifluoromethoxy)phenyl]-hydrazinecarboxamide (R-28153).

9. The method according to claim 8 wherein said composition is administered as a spot-on, pour-on, dip, wash, gel, shampoo, spray, foam, or lotion.

10. The method according to claim 8 wherein said animal is selected from the group consisting of dogs; cats; swine, cattle; horses; and sheep.

11. The method according to claim 10 wherein said ectoparasiticidal infection or infestation is caused by fleas, ticks, lice, mites or flies.

12. The method according to claim 8 wherein said composition is administered as a spot-on.

13. The method according to claim 12 wherein said animal is a dog or cat.

14. The method according to claim 13 wherein said ectoparasiticidal infection or infestation is caused by fleas or ticks.

15. The method according to claim 8 wherein said composition is administered as a pour-on.

16. The method according to claim 15 wherein said animal is swine, sheep or cattle.

17. The method according to claim 14 wherein the effective amount of amitraz is about 13-20% w/v and R-28153 is about 13-20% w/v.

18. The method according to claim 16 wherein the effective amount of amitraz is about 3-9% w/v and R-28153 is about 3-9% w/v.

19. A process for the preparation of a composition according to claim 1 which comprises: admixing N,N-diethyl-m-toluamide and γ-hexylactone, optionally with eucalyptol, dimethyl sulfoxide and 1-methoxy-2-propyl acetate to form a solvent mixture; and treating said solvent mixture with amitraz and 2-[2-(4-cyanophenyl)-1-[3-(trifluoromethyl)phenyl]ethylidene]-N-[4-(trifluoromethoxy)phenyl]-hydrazinecarboxamide (R-28153) to form a homogeneous solution, optionally passing said solution through a solid dehydrating agent.

20. The process according to claim 19 wherein the solid dehydrating agent is 4 Å molecular sieves.

* * * * *